United States Patent [19]

Kitao et al.

[11] Patent Number: 5,281,596
[45] Date of Patent: Jan. 25, 1994

[54] ANTIBACTERIAL DRUGS FOR FISH

[75] Inventors: Tadatoshi Kitao, Miyazaki; Noboru Sekiguchi; Toshio Hayami, both of Tokyo, all of Japan

[73] Assignee: Bayer Aktiengesellschaft, Leverkusen, Fed. Rep. of Germany

[21] Appl. No.: 725,370

[22] Filed: Jun. 27, 1991

Related U.S. Application Data

[63] Continuation of Ser. No. 614,565, Nov. 14, 1990, abandoned, which is a continuation of Ser. No. 12,985, Feb. 10, 1987, abandoned.

[30] Foreign Application Priority Data

Feb. 19, 1986 [JP] Japan .................. 61-32718

[51] Int. Cl.$^5$ .................. A61K 31/495; C07D 403/04
[52] U.S. Cl. .................. 514/254; 514/363; 546/146; 546/147
[58] Field of Search .................. 514/254

[56] References Cited

U.S. PATENT DOCUMENTS 4,659,603  4/1987  Grohe et al. .................. 514/254
4,670,444  6/1987  Grohe et al. .................. 514/254

FOREIGN PATENT DOCUMENTS 0219784  4/1987  European Pat. Off. .

OTHER PUBLICATIONS

Antimicrob. Agents Chemother., vol. 27, Nr. 6, 1985; pp. 966-967; Comparative In Vitro Activities of Selected Antimicrobial Agents Against Edward Siella Tarda; John J. Reinhardt et al.
John F. Reinhardt et al., Comparative In Vitro Activities of Selected Antimicrobial Agents Against Aeromonas Species and Plesiomonas Shigelloides; Antimicrob. Agents Chemother, vol. 27, Nv. 4, 1985, pp. 643-645.
J. F. M. Nouws et al., Pharmacokinetics of Ciprofloxacin in Carp., African Catfish and Rainbow Trout, Vet. Q., vol. 10, Nr. 3, Jul. 1988, pp. 211-216.
H. Knothe et al., Die Antibakterielle Aktivitat Von Ciprofloxacin, Ofloxacin und Norfloxacid Im Vergleich Zu Anderen Chemotherapeutika Gegenuber Enteropathogenen Bakterien, Fortchr. Antimikrob. Antioneoplast. Chemother., vol. 3, Nr. 5, (1984), pp. 615-620.
D. Flemingham et al., In Vitro Evaluation of Two New 4-Quinolones: S25930 and S25932, Recent Adv. Chemother., Proc. Int. Congr. Chemother., 14th, (1985), Antimicrobial Sect. 2., pp. 1521-1522.
M. D. Okare et al., The Comparative In Vitro Activity of Twelve 4-Quinolone Antimicrobials Against Enteric Pathogens, Drugs Exp. Clin. Res., vol. 11, Nr. 4, (1985), pp. 253-257.
H. Grimm, In-Virto-Aktivitaten Und Paralleiresistenz Von Gyrase-Hemmern, Forstchr. Antimikrob. Antineoplast. Chemother., vol. 3, Hr. 5., (1984), pp. 579-588.
Peterson, "Chemical Abstracts", vol. 106, (1987), Col. 106:112961c.
Endo, et al., "Chemical Abstracts", vol. 79, (1973), Cols. 123y and 124z.
Shimizu, et al., "Chemical Abstracts", vol. 83, (1975), Col. 152365z.
Komatsu, et al., "Chemical Abstracts", vol. 84, (1976), Cols. 84:26134f and 84:26136h.
Shimizu, et al., "Chemical Abstracts", vol. 85, (1976), Col. 85:87538h.

*Primary Examiner*—C. Warren Ivy
*Assistant Examiner*—James H. Turnipseed
*Attorney, Agent, or Firm*—Sprung Horn Kramer & Woods

[57] ABSTRACT

The method of combating bacterial infection of fish which comprises supplying to such fish or to their water an antibacterially effective amount of a quinoline derivative, salt or hydrate thereof of the formula

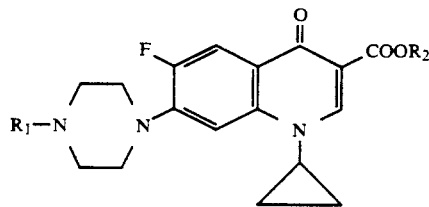

in which
  $R_1$ is hydrogen or a lower alkyl or lower hydroxy alkyl group, and
  $R_2$ is hydrogen or a lower alkyl group.

1 Claim, No Drawings

ANTIBACTERIAL DRUGS FOR FISH

This application is a continuation of application Ser. No. 614,565, filed Nov. 14, 1990, now abandoned, which is a continuation of Ser. No. 012,985, filed Feb. 10, 1987, now abandoned.

This invention relates to antibacterial drugs for fish. More particularly, the invention relates to antibacterial drugs useful for the prevention, cure and treatment of infectious diseases of fishes caused by microorganisms or aquatic microorganisms, which contain as the effective ingredient the quinoline derivatives, salts, or hydrates thereof represented by the general formula

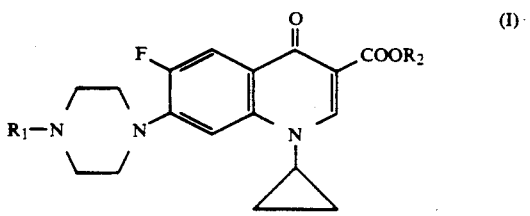

wherein $R_1$ represents a hydrogen atom, a lower alkyl or lower hydroxy alkyl group, and $R_2$ represents a hydrogen atom or a lower alkyl group.

Recently fish culture is more and more extensively carried on due to the 200-mile fishing zone exclusively and a fish shortage caused by overfishing. Accompanying this trend, efforts are being directed to high-efficiency fish production. Particularly in high-density cultivation fishery practiced with young yellowtails, eels, or the like, mass attack of infectious diseases in the fish occur with high frequency and, if such diseases are left untreated, the damage occasionally amounts to entire destruction of the fish in the culture farm. Even if the damage does not go so far, the surviving fish are spoiled and have markedly reduced commercial value. This type of problem is encountered at many places, and its early and effective solution has been strongly in demand.

The majority of infectious diseases of fish are caused by microorganisms or aquatic microorganisms, and for their prevention or cure heretofore it has been practiced to add antibacterial drugs such as sulfas, nitrofuran, synthetic penicillin, tetracycline, macrolide antibiotics, nalidixic acid, oxolinic acid, piromidic acid or chloroamphenicol to the feed for their oral administration to fish, or to put infected fish in water containing such antibiotics dissolved therein, a so-called medicated bath, for a predetermined period. However, heretofore such known antibacterial drugs exhibit such deficiencies as their antimicrobial spectra are narrow, low curative effect, safety margins (margin between the effective dose and toxic dose) are narrow, undesirable side-effects occur and their use is uneconomical.

It is found that the quinoline derivatives, their salts, and hydrates thereof expressed by the foregoing general formula (I) exhibit excellent preventive and curative effects broadly against various infectious diseases of fish caused by microorganisms and aquatic microorganisms, that they also are highly effective against resistant bacteria and complications, and furthermore that they have low toxicity, are safe and quick in metabolism, and are extremely suited for preventive and curative treatments for infectious diseases of fish.

Referring to aforesaid general formula (I), lower alkyl moieties in "lower alkyl" or "lower hydroxy alkyl" groups include straight chain or branched chain alkyl groups containing up to six carbon atoms, preferably up to four carbon atoms, e.g., methyl, ethyl, n-propyl, iso-propyl, n-butyl, sec-butyl, iso-butyl, tert-butyl, etc. And, preferred specific examples of $R_1$ include hydrogen, methyl, ethyl and β-hydroxyethyl groups. Also as $R_2$, hydrogen, methyl and ethyl groups are preferred.

Typical examples of the quinoline derivatives of formula (I) to be used as the effective ingredient in the antibacterial drug of this invention include the following:

1-Cyclopropyl-6-fluoro-1,4-dihydro-4-oxo-7-piperazinoquinoline-3-carboxylic acid, Methyl 1-cyclopropyl-6-fluoro-1,4-dihydro-4-oxo-7-piperazino-quinoline-3-carboxylate, Ethyl 1-cyclopropyl-6-fluoro-1,4-dihydro-4-oxo-7-piperazino-quinoline-3-carboxylate, 1-Cyclopropyl-6-fluoro-1,4-dihydro-4-oxo-(4-methylpiperazino)-quinoline-3-carboxylic acid, Ethyl 1-cyclopropyl-6-fluoro-1,4-dihydro-4-oxo-7-(4-methylpiperazino)4-quinoline-3-carboxylate, 1-Cyclopropyl-6-fluoro-1,4-dihydro-4-oxo-7-(4-ethylpiperazino)-quinoline-3-carboxylic acid, Ethyl 1-cyclopropyl-6-fluoro-1,4-dihydro-4-oxo-7-(4-ethylpiperazino)-quinoline-3-carboxylate, and 1-Cyclopropyl-6-fluoro-1,4-dihydro-4-oxo-7-(4-β-hydroxyethyl-piperazino)-quinoline-3-carboxylic acid.

The quinoline derivatives of formula (I) may be used in the form of acid addition salts utilizing the basicity of piperazino group at 7-position. Examples of such acid addition salts include inorganic acid salts such as hydrochloride, hydrobromide, hydroiodide and sulfate; and organic acid salts such as acetate, citrate, benzenesulfonate and embonate (pamoate). Again, when $R_2$ is a hydrogen atom, in the formula (I) quinoline derivatives the carboxyl group at 3-position may be in a salt form. As such salt, alkali metal salts such as sodium salt or potassium salt; alkaline earth metal salts such as magnesium salt or calcium salt; and ammonium salt, etc., are included.

Furthermore, the quinoline derivatives of formula (I) or salts thereof may be used in the form of their hydrates.

Most of the quinoline derivatives of formula (I) are the compounds known per se, as disclosed, for example, in Laid-Open Patent Applications, Kokai Nos. 71683/82 and 74667/83, and can be prepared by the methods described in those applications.

For administering the quinoline derivatives, salts thereof or hydrates thereof of formula (I) [hereinafter referred to as "active compounds of formula (I)"] to fish as antibacterial drugs, they may be blended in the fish feed to be orally administered, or may be dissolved in water in which sick fish are put and allowed to swim around (a method using a so-called "medicated bath").

The active compounds of formula (I) can be given the formulation form suitable for such method of administration, for example, powder, granule or solution as feed additives; or a soluble dispersant or solution for medicated bath. Methods for making such formulations per se are similar to those normally practiced for formulation of preventive and curative drugs for acute attack. In general practice one or more of various additives, e.g., excipients such as soybean protein, lactose, beer yeast and limestone; diluents such as water; solubilizing agents such as benzyl alcohol, n-butanol, etc.; thickener such as hydroxypropylmethyl cellulose, and pH-regulators such as potassium hydroxide, sodium hydroxide, tactic acid, hydrochloric acid and acetic acid, are suitably blended with the active compound of formula (I) to give the desired form of formulation. Hereinafter the typical forms will be more specifically explained.

| Formulation Example 1 (powder as feed additive): | |
|---|---|
| Active compound of formula (I) | 1–10 parts by weight |
| Soybean protein | 99–90 parts by weight |
| Total | 100 parts by weight |

Soybean protein is added to the active compound of formula (I), and homogeneously mixed in a mixer.

| Formulation Example 2 (solution as feed additive or for medicated bath): | |
|---|---|
| Active compound of formula (I) | 0.5–10 parts by weight |
| Potassium hydroxide | 0.08–1.5 parts by weight |
| Benzyl alcohol | 1.3–1.4 parts by weight |
| Hydroxypropylmethyl cellulose 50 | 0–3.5 parts by weight |
| Purified water | balance |
| Total | 100 parts by weight |

Potassium hydroxide is added to purified water and stirred until a homogeneous system is obtained, to which the active compound of formula (I), benzyl alcohol and hydroxypropylmethyl cellulose 50 were added and stirred to uniformity.

| Formulation Example 3 (soluble powder for medicated bath): | |
|---|---|
| Active compound of formula (I) (water-soluble) | 1–10 parts by weight |
| Lactose | 99–90 parts by weight |
| Total | 100 parts by weight |

Lactose is added to the active compound of formula (I), and homogeneously mixed in a mixer.

In the use of active compound of formula (I) as the antibacterial drug for fish, the administration dosage differs depending on the purpose of administration (prevention or cure of disease) and type, size and extent of infection of the object fish to be treated. Normally, however, the dosage within 5–1000 mg, preferably 20–100 mg, per kg of body weight of fish may be administered per day, either at one time or as divided into several times. Needless to explains, however, the above dosage is a rough standard, which may be reduced or increased depending on age, body weight, condition of disease, etc. of the object fish. The term of administration is not particularly limited, but normally 1–about 10 days can achieve sufficient effect.

The antibacterial drugs provided by the present invention are broadly active against various microorganisms and aquatic microorganisms which induce infectious diseases among fish. For example, the drugs exhibit powerful antibacterial action against bacteria belonging to genus Aeromonas, genus Edwardsiella, genus Pasteurella, genus Pseudomonas, genus Streptococcus and genus Vibrio, and consequently are extremely useful for prevention, cure and treatment of infectious diseases of cultivated fresh-water and seawater fish such as young yellowtails, yellowtails, eels, ayus, trout, salmon carps, etc. and of aquarium fish such as goldfish and tropical fish.

Such excellent activities of the antibacterial drugs of the present invention are proven by the following in vitro and in vivo tests in which the following compounds were used.

Compound A: hydrochloride of 1-cyclopropyl-6-fluoro-1,4-dihydro-4-oxo-7-piperazino-quinoline-3-carboxylic acid (decomposition point: 319°–321° C.)

Compound B: monohydrate of hydrochloride of 1-cyclopropyl-6-fluoro-1,4-dihydro-4-oxo-7-piperazino-quinoline-3-carboxylic acid Compound C: hydrochloride of 1-cyclopropyl-6-fluoro-1,4-dihydro-4-oxo-7-(4-methylpiperazino)-quinoline-3-carboxylic acid (decomposition point: 345°–347° C.)

Compound D: 1-cyclopropyl-6-fluoro-1,4-dihydro-4-oxo-7-(4-ethylpiperazino)-quinoline-3-carboxylic acid Compound E: dihydrate of hydrochloride of 1-cyclopropyl-6-fluoro-1,4-dihydro-4-oxo-7-(4-ethylpiperazino)-quinoline-3-carboxylic acid Compound F: hydrochloride of 1-cyclopropyl-6-fluoro-1,4-dihydro-4-oxo-7-(4-$\beta$-hydroxyethylpiperazino)-quinoline-3-carboxylic acid (decomposition point: 327°–333° C.)

Compound G: embonate of 1-cyclopropyl-6-fluoro-1,4-dihydro-4-oxo-7-(4-ethylpiperazino)-quinoline-3-carboxylic acid Compound H: ethyl 1-cyclopropyl-6-fluoro-1,4-dihydro-4-oxo-7-(4-ethylpiperazino)-quinoline-3-carboxylate (decomposition point: 187°–189° C.)

Compound OA (control): 1-ethyl-1,4-dihydro-6,7-methylenedioxy-4-oxo-3-quinolinecarboxylic acid.

Test Example 1

In vitro antibacterial activity on pathogenic-bacteria for fish

Each of the test strains was cultured over-night, and each culture broth (containing about $10^6$ cells/ml) was inoculated in Mueller-Hinton agar (DIFCO) supplied with 1.0–2.0% sodium chloride and containing the test compound at each specified concentration. The minimum growth-inhibition concentration (MIC) was determined for each compound after 20 hours' incubation at 25°–30° C. The results were as shown in Table 1 below.

TABLE 1

| Test bacteria | In vitro Antibacterial Activity Against Pathogenic Bacteria for Fish (MIC, µg/ml) | | | | | | | | Control |
|---|---|---|---|---|---|---|---|---|---|
| | Compound | | | | | | | | |
| | A | B | C | D | E | F | G | H | OA |
| *Pasteurella piscicida* | | | | | | | | | |
| EH8304 | 0.05 | 0.025 | 0.05 | 0.05 | 0.05 | 0.1 | 0.1 | 25.0 | 0.1 |
| EH8309 | <0.025 | <0.0125 | 0.05 | 0.025 | 0.05 | 0.1 | 0.1 | 25.0 | 0.1 |
| EH8312 | 0.05 | 0.025 | 0.05 | 0.05 | 0.05 | 0.1 | 0.05 | 12.5 | 0.1 |

TABLE 1-continued

In vitro Antibacterial Activity Against Pathogenic Bacteria for Fish (MIC. μg/ml)

| Test bacteria | Compound A | B | C | D | E | F | G | H | Control OA |
|---|---|---|---|---|---|---|---|---|---|
| EH8313 | 0.0.5 | 0.025 | 0.05 | 0.05 | 0.05 | 0.1 | 0.05 | 12.5 | 0.1 |
| NG8319 | <0.025 | 0.025 | 0.05 | 0.025 | 0.05 | 0.1 | 0.01 | 25.0 | 0.1 |
| *Vibrio anguillarum* | | | | | | | | | |
| NH8410 | <0.025 | 0.025 | <0.025 | 0.025 | 0.05 | 0.1 | 0.05 | 12.5 | 0.05 |
| NA8340 | <0.025 | 0.025 | <0.025 | 0.025 | 0.05 | 0.1 | 0.05 | 25.0 | 0.05 |
| NA8341 | <0.025 | 0.025 | <0.025 | 0.025 | 0.05 | 0.1 | 0.05 | 25.0 | 0.05 |
| NA8346 | <0.025 | 0.025 | <0.025 | 0.025 | 0.05 | 0.1 | 0.05 | 12.5 | 0.05 |
| NA8347 | <0.025 | 0.025 | <0.025 | 0.025 | 0.05 | 0.05 | 0.05 | 12.5 | 0.05 |
| *Aeromonas hydrophila* | | | | | | | | | |
| KA8301 | <0.025 | <0.0125 | <0.025 | 0.025 | 0.05 | 0.05 | 0.05 | 12.5 | <0.0125 |
| KA8414 | <0.025 | <0.0125 | <0.025 | <0.0125 | <0.025 | <0.025 | 0.05 | 25.0 | <0.0125 |
| KA8416 | <0.025 | <0.0125 | <0.025 | <0.0125 | <0.025 | <0.025 | 0.05 | 12.5 | <0.0125 |
| M 183 | <0.025 | <0.0125 | <0.025 | <0.0125 | <0.025 | <0.025 | 0.05 | 12.5 | <0.0125 |
| C 44 | <0.025 | <0.0125 | <0.025 | <0.0125 | <0.025 | <0.025 | 0.05 | 50.0 | <0.0125 |

Test Example 2

In vitro antibacterial activity of Compound D against Various Pathogenic Bacteria for Fish Each of the test strains was cultured over-night, and the resultant culture broth (containing about $10^6$ cells/ml) was innoculated in Mueller-Hinton agar (DIFCO) supplied with 1.0-2.0% sodium chloride and containing the test compound at the specified concentration. The minimum growth-inhibition concentration (MIC) was determined for each compound after 20 hours' incubation at 25°-30° C. The results were as shown in Table 2 below.

TABLE 2

In vitro Antibacterial Activity of Compound D against Pathogenic Bacteria for Fish

| Test bacteria | Number of strains | MIC (μg/ml) Compound D | Oxolinic acid |
|---|---|---|---|
| *Aeromonas hydrophila* | 25 | <0.125-0.05 | <0.0125-0.025 |
| *Aeromonas salmonicida* | 25 | 0.0125-0.1 | 0.05-3.2 |
| *Edwardsiella tarda* | 25 | 0.025-0.2 | 0.05-1.6 |
| *Pasteurella piscicida* | 25 | <0.0125-0.05 | 0.025-0.1 |
| *Pseudomonas anguilliseptica* | 18 | <0.0125-0.025 | <0.0125-0.05 |
| *Streptococcus* sp. | 25 | 0.8 | 200-400 |
| *Vibrio anguillarum* | | | |
| Yellowtail origin | 25 | 0.05-0.1 | 0.025-0.05 |
| Ayu origin | 25 | 0.025-0.4 | 0.05-25 |

Of those active compounds used in the above test examples, a production example of compound H is shown hereinbelow for reference.

Production Example 1

Into a suspension of 18 g of 1-cyclopropyl-7-(4-ethyl-1-piperazinyl)-6-fluoro-1,4-dihydro-4-oxo-quinoline-3-carboxylic acid in 120 ml of ethanol, 24 g of 96% conc. sulfuric acid was added dropwise. The resulting mixture was refluxed for 12 hours, and after removing excessive alcohol under a reduced pressure, the remainder was dissolved in 200 ml of ice water. Under cooling with ice, the pH of the system was rendered 12-14 by addition of a cold solution of 19.2 g of sodium hydroxide in 100 ml of water, and the precipitate formed in the meantime was suction-filtered. The precipitate was then washed with water and dried at 100° C. under a reduced pressure. Upon recrystallizing the same from toluene/light benzene, 10 g of ethyl ester of 1-cyclopropyl-7-(4-ethyl-1-piperazinyl)-6-fluoro-1,4-dihydro-4-oxo-quinoline-3-carboxylic acid (52.5% of the theoretical amount) melting at 187°-189° C. was obtained.

It will be understood that the specification and examples are illustrative but not limitative of the present invention and that other embodiments within the spirit and scope of the invention will suggest themselves to those skilled in the art.

What is claimed is:

1. The method of combating bacterial infection of fish which comprises supplying to such fish or to their water an antibacterially effective amount of 1-cyclopropyl-6-fluoro-1,4-dihydro-4-oxo-7-(4-ethyl-piperazino)-quinoline-3-carboxylic acid, or a salt or hydrate thereof, wherein the effective amount is 5 to 100 mg, per kg of body weight of fish per day.

* * * * *